United States Patent [19]

Isakozawa et al.

[11] Patent Number: 5,142,149

[45] Date of Patent: Aug. 25, 1992

[54] ELECTRON MICROSCOPE

[75] Inventors: Shigeto Isakozawa, Katsuta; Hiroyuki Kobayashi, Mito, both of Japan

[73] Assignee: Hitachi, Ltd., Tokyo, Japan

[21] Appl. No.: 552,456

[22] Filed: Jul. 16, 1990

[30] Foreign Application Priority Data

Jul. 19, 1989 [JP] Japan .................................. 1-187056

[51] Int. Cl.⁵ .......................................... H01J 37/252
[52] U.S. Cl. ................................... 250/311; 250/310; 250/306
[58] Field of Search ................ 250/311, 310, 306, 307

[56] References Cited

U.S. PATENT DOCUMENTS 4,633,085 12/1986 Tomita et al. ...................... 250/311

FOREIGN PATENT DOCUMENTS 0202937 11/1986 European Pat. Off. .

OTHER PUBLICATIONS

Watt, Journal of Physics E. Scientific Instruments, vol. 19, No. 9, Sep. 1986, pp. 668–678.
Wintsch et al., Mikrochimica Acta, I, 1982, pp. 63–72.

*Primary Examiner*—Jack I. Berman
*Attorney, Agent, or Firm*—Antonelli, Terry, Stout & Kraus

[57] ABSTRACT

A sample is irradiated with an electron beam and analyzed by detecting characteristics X-rays obtained from the sample and electron beams transmitted thereby. There is provided means, which collects analysis results obtained by this analysis to compare the analysis results thus collected.

4 Claims, 5 Drawing Sheets

ELECTRON MICROSCOPE

BACKGROUND OF THE INVENTION

1. Field of the Invention

The present invention relates to an electron microscope and in particular to an electron microscope provided with a plurality of analyzing apparatuses.

2. Description of the Related Art

An electron microscope is often provided with an apparatus for analyzing the energy of an electron beam, which has been transmitted by a sample while irradiating the sample with the electron beam, and an apparatus for analyzing characteristic X-rays generated by the sample while irradiating the sample with the incident electron beam. Since the apparatus analyzing the energy of transmitted electrons and the apparatus analyzing the energy of characteristic X-rays give sorts of information different from each other, it is possible to effect a many-faceted element analysis of the sample in addition form observation thereof by means of such an electron microscope provided with a plurality of analyzing apparatuses.

Qualitative and quantitative analysis of sodium (Na: atomic number 11) to uranium (U: atomic number 92) can be effected by using the apparatus analyzing the energy of characteristic X-rays. On the other hand, by using the apparatus analyzing the energy of transmitted electrons it is possible to detect easily light elements such as lithium (Li: atomic number 3) to heavy elements and further to obtain information on the binding state of elements. However there are elements which are difficult to detect.

SUMMARY OF THE INVENTION

An object of the present invention is to provide an electron microscope suitable for facilitating the comparison between results of analyses obtained by means of different sorts of analyzing apparatuses.

Another object of the present invention is to provide an electron microscope suitable for facilitating the manipulation of different sorts of analyzing apparatuses.

An electron microscope according to the present invention comprises means for producing an electron beam; means for irradiating the sample with the electron beam; a plurality of sorts of analyzing means for detecting signals obtained by irradiating the sample with the electron beam to effect analysis of the sample, and means for collecting results of analyses of the sample obtained by using these analyzing means to compare the results of analyses thus obtained.

Other objects and features of the present invention will be clear from following explanation made while referring to the drawings.

DESCRIPTION OF THE PREFERRED EMBODIMENTS

Figure 1:
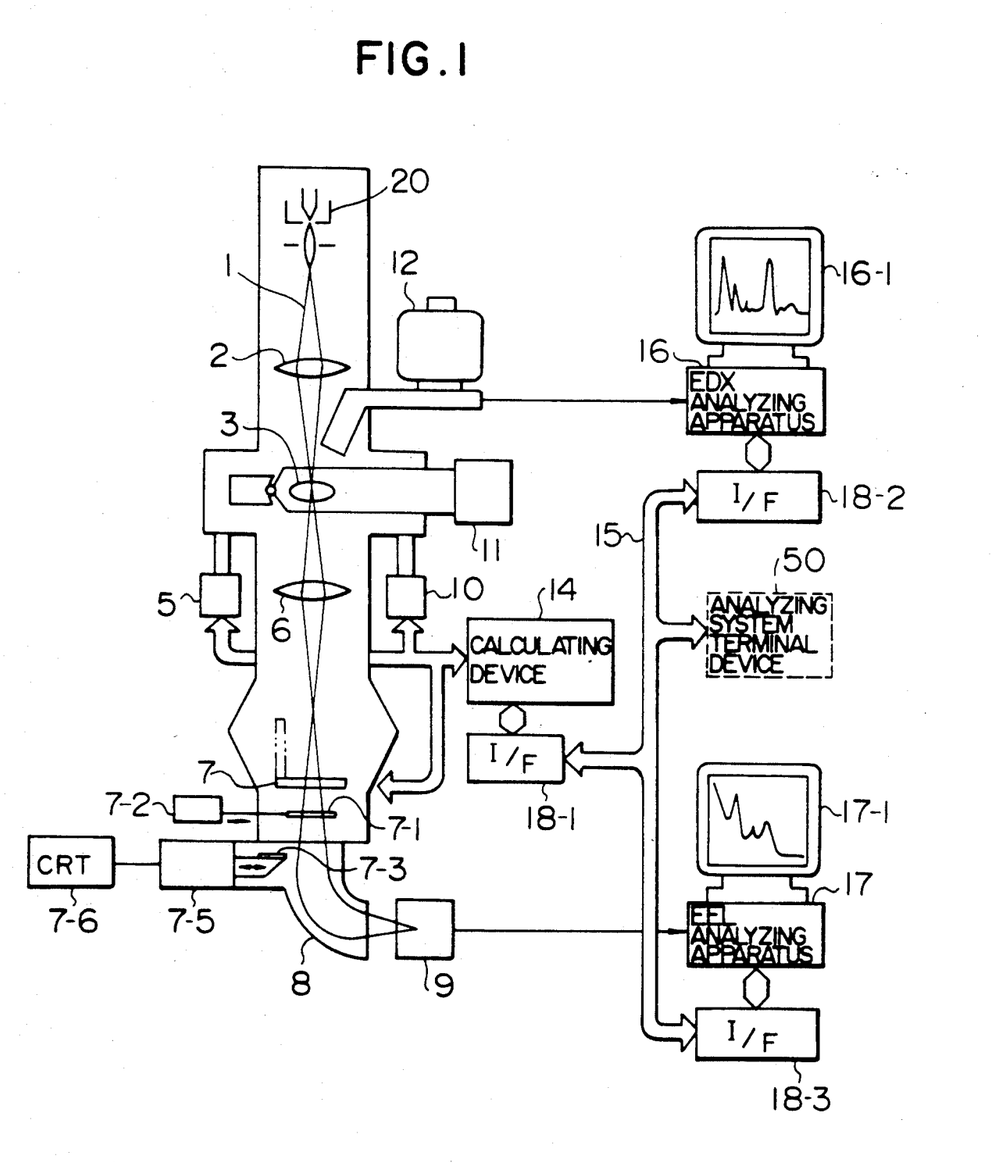
FIG. 1 is a scheme showing the conception of an electron microscope, which is an embodiment of the present invention.

Referring to FIG. 1, an electron beam 1 emitted by an electron gun 20 is focused on a sample 3 by a focusing lens system 2 to irradiate the sample therewith. The sample 3 is held by a sample holder 11 and characteristic X-rays having energies proper to the elements constituting the sample are generated by irradiating the sample 3 with the electron beam. The generated characteristic X-rays are detected by an X-ray detector 12 and analyzed the energy thereof by means of an energy dispersive X-ray analyzing apparatus (hereinbelow called EDX analyzing apparatus) 16 having memory means. Results thus obtained are expressed by an X-ray spectrum, in which the abscissa represents the energy and the ordinate the X-ray intensity. The EDX analyzing apparatus 16 prints out identified elements.

On the other hand, the electron beam transmitted by the sample 3 is analyzed as to the energy thereof by an energy analyzing apparatus 8 through another focusing lens system 6 and an electron beam having a specified energy is detected by a detector 9. The energy analyzing apparatus 8 includes magnetic field generating means for analyzing the energy and electron beams having various energies are detected one after another by the detector 9 by sweeping the intensity of the magnetic field generated by this magnetic field generating means. The output of the detector 9 is led to an electron energy loss analyzing apparatus (hereinbelow called EEL analyzing) 17 including memory means, which apparatus displays an energy spectrum of the electron beam in a display device 17-1, in which the abscissa represents the energy and the ordinate represents the intensity of the electron beam, and at the same time prints out the identified elements.

When an enlarged image (transmission electron microscope image) of the sample 3 in obtained by using the electron beam transmitted by the sample 3, a fluorescent plate 7 is displaced to a position, where it is exposed to the transmitted electron beam. In this way, the electron beam transmitted by the sample 3 is enlarged by the focusing lens system 6 and projected onto the fluorescent plate 7. The fluorescent plate 7 transforms the enlarged image of the electron beam into a visible enlarged image.

When a photographic film or photographic plate 7-1 is moved by a driving device 7-2 to a position where it is exposed to the electron beam, and the fluorescent plate 7 is removed from the axis of the electron beam, the electron microscope image is photographed.

When the fluorescent plate 7 and the film or plate 7-1 are removed from the axis of the electron beam and another fluorescent plate 7-3 is moved to a position, where it is exposed to the electron beam, the electron microscope image produced on the fluorescent plate 7-3 is transformed into a visible image, which is imaged by a television camera 7-5 and displayed on a cathode ray tube 7-6.

The sample 3 can be finely displaced in the horizontal direction on by means of an X actuator 5 and a Y actuator 10, i.e. fine adjustment in the X and the Y direction is possible. The actuators 5 and 10 are connected with a calculating device 14 and the coordinates representing the position, where the sample 3 displaced by the activators 5 and 10 is observed, are inputted in the calculating device 14.

Standard interfaces 18-1, 18-2 and 18-3 of common specification are incorporated in the calculating device 14, the EDX analyzing apparatus 16 and the EEL analyzing apparatus 17, respectively and transmission and reception of various sorts of information are freely executed between different apparatuses through a common bus 15.

An analyzing system terminal device 50 indicated by a broken line will be explained later as another embodiment of the present invention.

Figure 2:
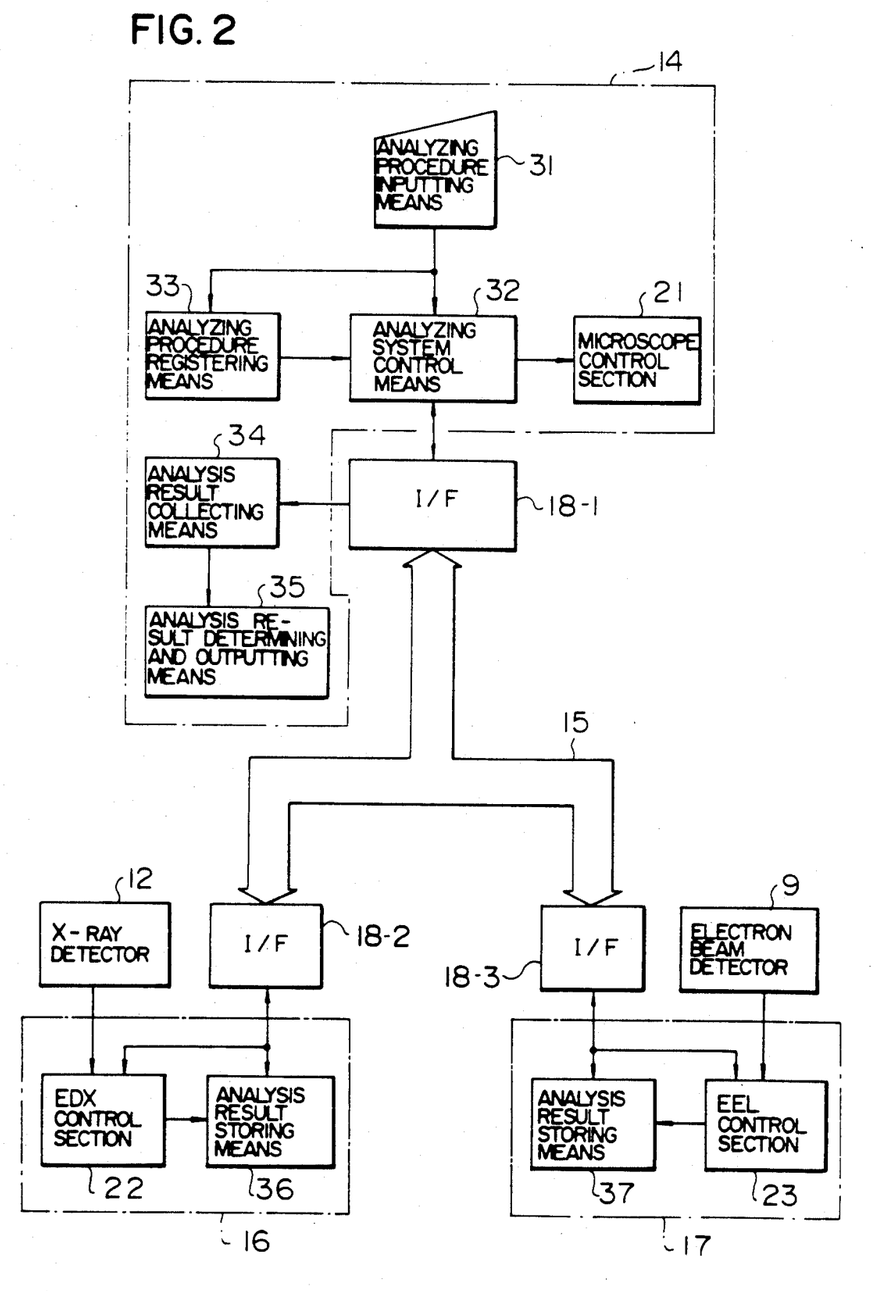
FIG. 2 is a block diagram of the principal part of the electron microscope indicated in FIG. 1.

FIG. 2 is a block diagram indicating an embodiment of the construction of the principal part of the calculating device 14, the EDX analyzing apparatus 16 and the EEL analyzing apparatus 17 in a concrete manner.

In the figure, the calculating device 14 is composed of analyzing procedure, inputting means 31, in which the analyzing procedure such as positions to be analyzed and the order of analysis is inputted; analyzing procedure registering means 33, which registers the inputted analyzing procedure; a microscope control section 21, which controls the operation of the electron microscope; analysis result collecting means 34 collecting analysis results obtained by the other analyzing apparatuses, which are inputted through the interface 18-1; analysis result determining and outputting means 35, which compares various analysis results collected by the analysis result collecting means 34 to determine the final analysis result and output it; and analyzing system control means 32, which controls these means according to the analyzing procedure, as stated later in detail.

The EDX analyzing apparatus 16 is composed of an EDX control section 22 effecting the analysis on the basis of detected signals coming from X-ray detector 12 and analysis result storing means 36, which stores the analysis result.

The EEL analyzing apparatus 17 is composed of an EEL control section 23 effecting analysis on the basis of detected signals coming from an electron beam detector 9 and analysis result storing means 37, which stores the analysis result.

Figure 3:
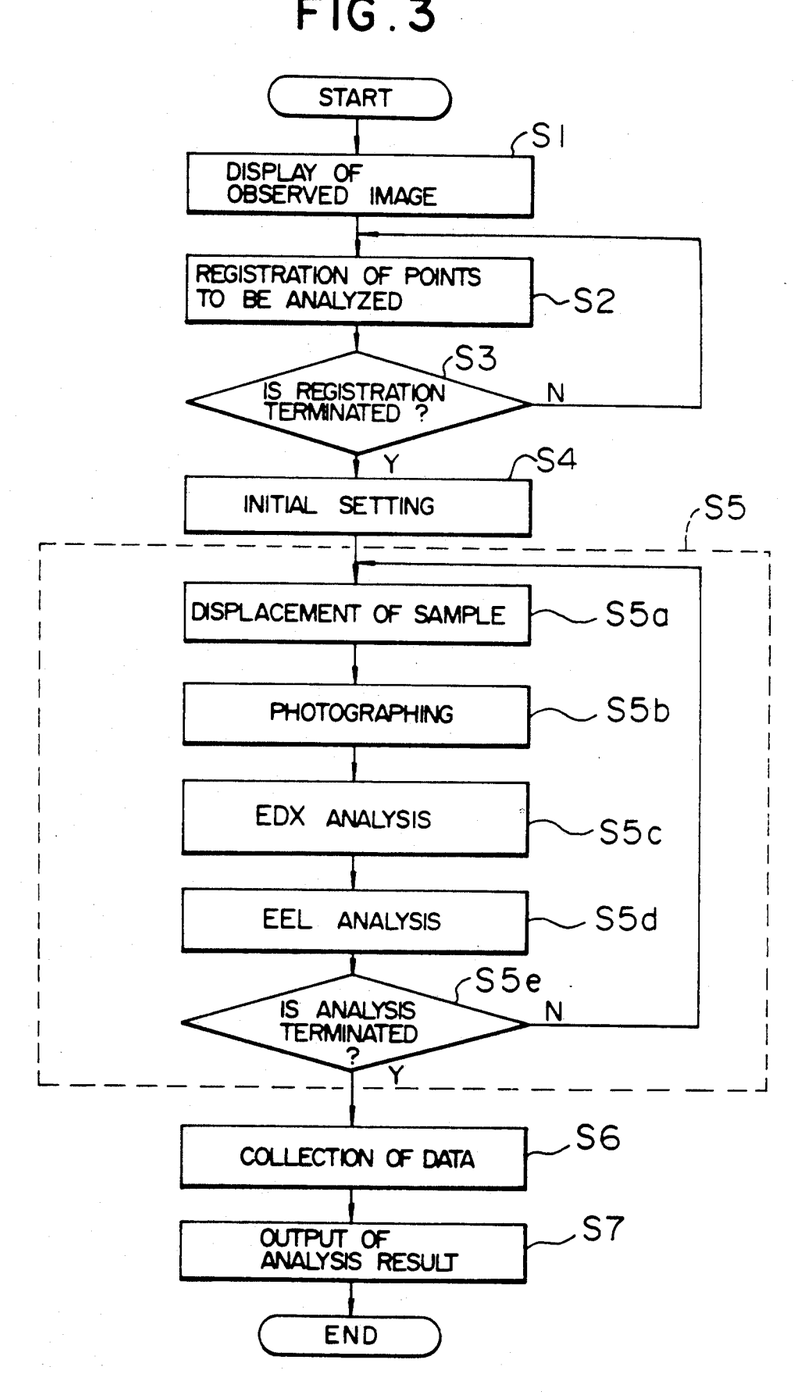
FIG. 3 is a working flow chart of the electron microscope indicated in FIG. 1.

An analyzing method using the analyzing system having such a structure will be explained, referring to the flow chart indicated in FIG. 3.

Figure 4:
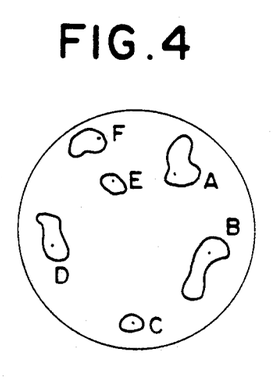
FIG. 4 is a scheme of an electron microscope image obtained by means of the electron microscope indicated in FIG. 1.

In Step S1, in order to register previously the coordinates of all the points to be analyzed on the sample 3, the sample is irradiated with an electron beam having a relatively great spot diameter (several tenth micron) to display an electron microscope image of the sample on the cathode ray tube 7-6. FIG. 4 shows a simplified image of the sample displayed on the cathode ray tube. In the present embodiment, it is supposed that there are six points A, B, C, D, E and F to be observed. The sample is usually circular, with a diameter of about 3 mm. In the figure, the dot indicates a position to be irradiated with a focused electron beam.

When such an image of the sample is displayed, in Step S2, an operator drives at first the actuators 5 and 10 by manipulating the analyzing procedure inputting means 31 so that the point A to be analyzed is at the point indicated by the dot. At this time the coordinates of the actuators 5 and 10 are registered in the analyzing procedure registering means 33. A position, at which the object is to be analyzed can be determined relatively easily by observing the image with a low magnification factor, and the displacement of the position to be irradiated to the analyzed position is also extremely easy with respect to that required for an observation with a high magnification factor.

In Step S3, it is judged whether the registration of coordinates for all the points to be analyzed is terminated or not. In the case where it is not terminated, the procedure returns to Step S2. Thereafter, in the same way, the positions of coordinates for all the points to be analyzed B, C, . . . , F are registered in the analyzing procedure registering means 33. At this time, the specification whether each of the points to be analyzed should be analyzed or not is also carried out by manipulating the analyzing procedure inputting means 31.

When the registration of the coordinates of all the points to be observed is terminated, in Step 4, information for the initial setting of the EDX analyzing apparatus 16 and the EEL analyzing apparatus 17 is inputted by using the analyzing procedure inputting means 31. The inputted information described above is outputted to the common bus though the interface 18-1 after having been transformed into electric signals by the analyzing system control means 32.

The signals outputted in the common bus 15 are inputted further in the EDX analyzing apparatus 16 and the EEL analyzing apparatus through the interfaces 18-2 and 18-3, respectively. In the EDX analyzing apparatus and the EEL analyzing apparatus, the EDX control section 22 and the EEL control section 23 are set at their initial state, responding to the inputted signals.

When the registration of the coordinates of the positions to be observed and the initial setting of the different analyzing apparatuses are completed and the start of the analysis is indicated by the operator, in Step S5, a series of observing and analyzing operations are executed, as explained below.

In Step S5a, the analyzing system control means 32 in the calculating apparatus 14 controls the microscope control section 21, depending on the coordinate information of the points to be analyzed registered in the analyzing procedure registering means 33. The microscope control section 21 drives the actuators 5 and 10, depending on the respective coordinate information. In this way, the sample 3 is displaced so that the point A to be analyzed as described above is irradiated with the electron beam at the beginning.

When the sample 3 arrives at the predetermined position, in Step S5b, the analyzing system control means 32 checks whether a photographing is specified or not, on the basis of the analyzing procedure described above. In the case where it is specified, the fluorescent plate 7 is opened by the microscope control section 21 and the electron beam is projected on the photographic film or plate 7-11 so that the photographing is effected.

When the photographing is terminated, in Step S5c, the electron beam is focused finely and projected on the point to be analyzed A by the microscope control section 21. Further an analysis start signal is outputted from the analyzing system control means 32 to the EDX analyzing apparatus 16 through the interfaces 18-1 and 18-2 and characteristic X-rays generated at this time at the point to be analyzed A are detected by the X-ray detector 12.

The detection, signal thus obtained is inputted in the EDX control section 22. The EDX control section 22 displays the X-ray spectrum corresponding to the detections signal a on the display device 16-1 and at the same time stores the result of the analysis, i.e. the element, which is analyzed, in the analysis result storing means 36 composed of a memory or a floppy disk.

In Step S5d, an analysis start signal is outputted from the analyzing system control means 32 to the EEL control device 17 through the interfaces 18-1 and 18-3 and the electron beam transmitted by the sample 3 is detected by the electron beam detector 9 after having been analyzed by the energy analyzing apparatus 8. The detection signal thus obtained is inputted in the EEL control section 23. The EEL control section 23 displays the energy spectrum of the electron beam on the display device 17-1 and at the same time stores the result of the analysis in the analysis result storing means 37.

When the analysis for the point A to be analyzed is completed in this way, the analyzing system control means 32 judges whether the analysis is completed for all the points to be analyzed or not. In the case where it is not completed, the procedure returns to Step S5a and the actuators 5 and 10 are driven, depending on the coordinate information of all the other points to be analyzed as registered for the analyzing procedure. In the same way the analysis of the other points B, C, ..., F it is effected. The analysis results are stored in the respective analyzing apparatuses.

Figure 5:
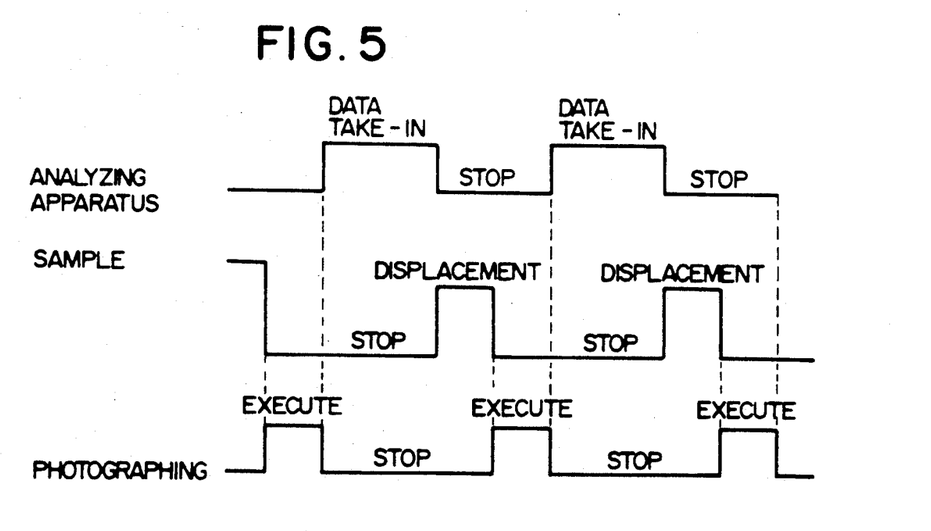
FIG. 5 is a chart showing the timing of analysis, sample displacement and photographing.

FIG. 5 is a chart indicating the timings of a series of the displacement of the sample, the photographing and the taking-in of detection data.

When the analysis is terminated in this way for all the points to be analyzed, in Step S6, the analysis results for every point to be analyzed stored in the analysis result storing means 36 of the EDX analyzing apparatus 16 and the analysis result storing means 37 of the EEL analyzing apparatus 17 are collected through the respective interfaces and stored in the analysis result collecting means 34.

In Step S7, the analysis result determining and outputting means 35 compares these collected analysis results with each other to obtain the final analysis result and to print out it. That is, if the analysis result obtained by the EDX analysis indicates Na and Ge and that obtained by the EEL analysis Li, B, Na and Ca, the final analysis result obtained as the result of the comparison is Li, B, Na, Ca and Ge which are printed out.

According to the present embodiment:

(1) since all the analyzing apparatuses can be controlled by the calculating device 14, a plurality of sorts of apparatuses can be controlled all together, which improves the operability, (2) since the analysis results of the various analyzing apparatuses are collected at one place and the final analysis result is obtained by comparing the collected analysis results with each other, a precise analysis can be effected without troubling any operator; and (3) since the analysis is effected automatically for a plurality of positions on a sample, the period of time, during which the operator is bound thereon, is shortened.

Further, although explanation has been made in the above embodiment, supposing that the analyzing procedure is prepared by manipulating the calculating device 14 and that the output of the operation instruction, the storage of the analysis results, the comparison of the analysis results, etc. for the various analyzing apparatuses are effected also by the calculating device 14 on the basis of the analyzing procedure, the present invention is not restricted thereto, but it is conceivable to adopt the following forms.

Figure 6:
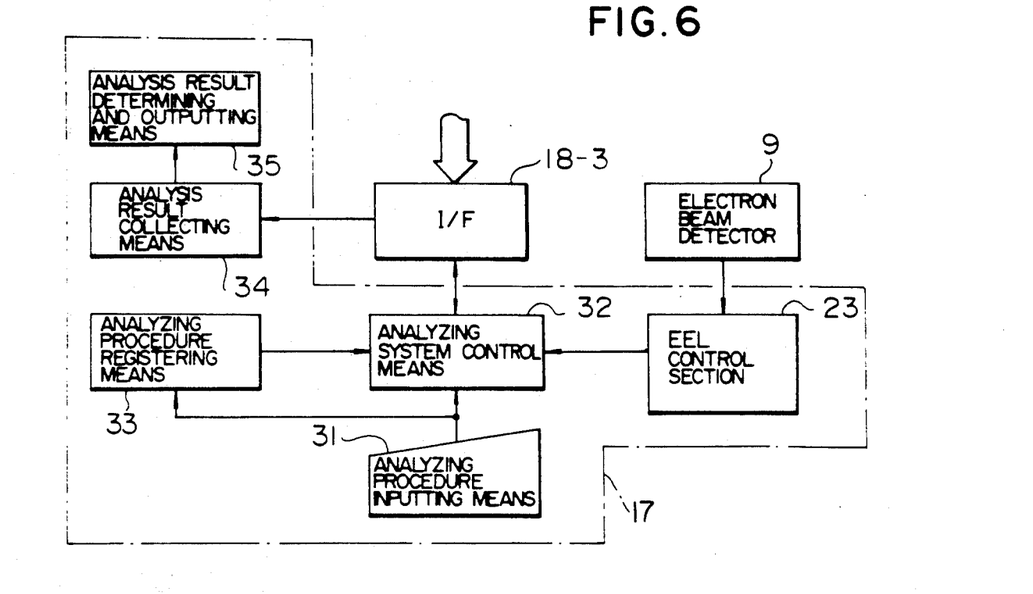
FIG. 6 is a block diagram showing another embodiment of the EEL analyzing apparatus indicated in FIG. 2.

FIG. 6 is a scheme for explaining another embodiment. Since the present embodiment is characterized particularly in the construction of the EEL analyzing apparatus 17, only a block diagram showing the construction of the principal part of the EEL analyzing apparatus 17 is indicated here.

In the present embodiment, the EEL analyzing apparatus 17 is composed of the EEL control section 23, the analyzing procedure inputting means 31, the analyzing system control means 32, the analyzing procedure registering means 33, the analysis result collecting means 34 and the analysis result determining and outputting means 35. The function of each of the means is identical to that explained, with reference to FIG. 2.

In the EEL analyzing apparatus thus constructed, the analyzing procedure is prepared by manipulating the analyzing procedure inputting means 31, which analyzing procedure is registered in the analyzing procedure registering means 33. When the starting of analysis is instructed by the operator, various sorts of control signals corresponding to the analyzing procedure are outputted from the analyzing system control means 32 to the common bus 15 through the interface 18-3 and thereafter they are outputted to the calculating device 14.

The calculating device 14, which has received the control signals, moves the sample, depending on the content thereof and outputs a displacement termination signal to the common bus 15 through the interface 18-1, when the sample arrives at a predetermined position.

The analyzing system control means 32 in the EEL analyzing apparatus 17 outputs an analysis start instruction to the EDX analyzing apparatus 16 through the interface 18-3, when the displacement termination signal is inputted therein. The EDX analyzing apparatus 16, which has received the analysis start instruction, detects the specified X-ray in the same way as described above and stores the analysis result.

When the analysis is completed, the EDX analyzing apparatus 16 outputs an analysis termination signal to the common bus 15 through the interface 18-2. The analyzing system control means 32, which has received the analysis termination signal through the interface 18-3, controls the EEL control section 23 to make it execute the analysis by itself, when it receives the analysis result, it stores the analysis result in the analysis result collecting means 34.

When the analysis is completed in this way for all the points to be analyzed, the analysis results stored in the EDX analyzing apparatus 16 are collected for every point to be analyzed through the interfaces and stored in the analysis result collecting means 34.

The analysis result determining and outputting means 34 compares the analysis result obtained by means of the EDX analyzing apparatus 16 and that obtained by means of the EEL analyzing apparatus 17 thus collected with each other to obtain the final analysis result and to point it out.

As it can be clearly seen from the above explanation, in the present embodiment, since the EEL analyzing apparatus 17 takes charge of all the control of the system, it is sufficient for the calculating device 14 to have only the means for displacing the sample stage, responding to the control signal coming from the EEL analyzing apparatus 17, and the analyzing procedure inputting means 31, the analyzing system control means 32, the analyzing procedure registering means 33, the analysis result collecting means 34 and the analysis result determining and outputting means 35, as explained reference to FIG. 2, are unneccessary.

Further, in the present embodiment, it is possible also to read out the analysis result obtained by means of the EDX analyzing apparatus 16 as needed to display it suitably on the display device 17-1 of the EEL analyzing apparatus 17.

Figure 7:
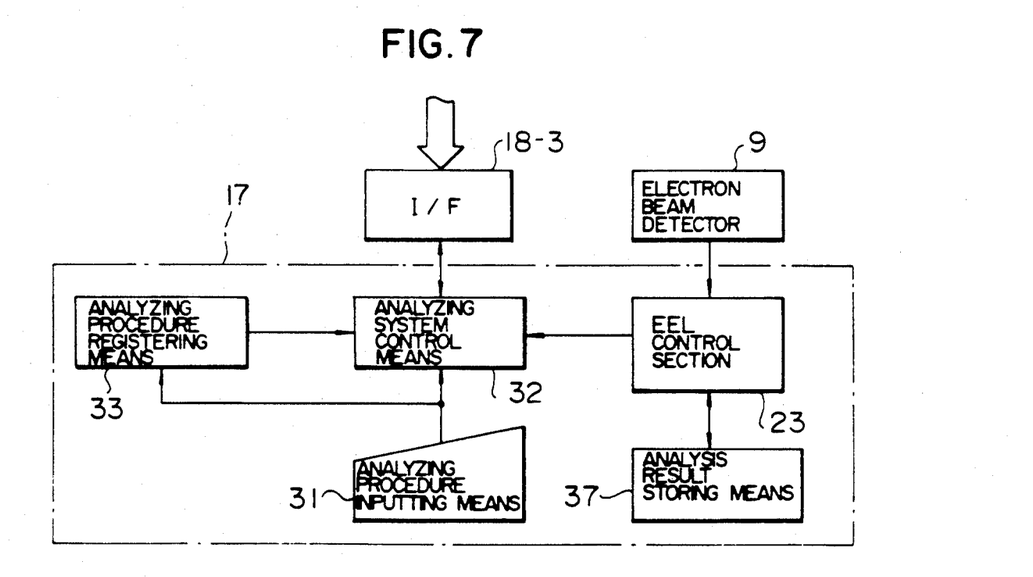
FIG. 7 is a block diagram showing still another embodiment of the EEL analyzing apparatus indicated in FIG. 2.

FIG. 7 is a scheme for explaining still another embodiment of the present invention. Since the present embodiment is characterized also particularly in the construction of the EEL analyzing apparatus, only a block diagram showing the construction of the principal part of the EEL analyzing apparatus 17 is indicated in the figure.

In the present embodiment, the EEL analyzing apparatus 17 is composed of the EEL control section 23, the analyzing procedure inputting means 31, the analyzing system control means 32, the analyzing procedure registering means 33 and the analysis result storing means 37.

In the EEL analyzing apparatus thus constructed, the analyzing procedure is prepared by manipulating the analyzing procedure inputting means 31 and is registered in the analyzing procedure registering means 33 in the same way as described previously. When the analysis start is instructed by the operator, various sorts of control signals according to the analyzing procedure are outputted from the analyzing system control means 32 to the common bus 15 through the interface 18-3 and thereafter they are outputted to the calculating device 14.

Here, in the present embodiment, not only the analysis result obtained by means of the EDX analyzing apparatus but also the analysis result obtained by means of the EEL analyzing apparatus are collected by the calculating device 14 through the interfaces. The calculating device 14, in which the analysis results are collected, compares them with each other to output the final analysis result.

As described above, in the present embodiment, the various controls for carrying out the analysis are effected by the EEL analyzing apparatus and the processings such as the collection of the analysis results, the comparison of the different analysis results etc. are executed by the calculating device 14.

Consequently, in comparing the present embodiment with that explained, with reference to FIG. 2, it is unnecessary for the calculating device 14 to be provided with the analyzing procedure inputting means 31 and the analyzing procedure registering means 33.

Further, although, in the embodiment described above, explanation has been made, on the assumption that the analysis result for each of the points to be analyzed is initially stored in each of the analyzing apparatuses and thereafter the analysis results are collected all together, they may be collected for every point to be analyzed.

Furthermore, as indicated by the broken line in FIG. 1, an analyzing system terminal device 50 constituted by a personal computer, etc., which has a function of controlling the analyzing system, may be connected with the interfaces described above so that the various kinds of controls, the storing of the analysis results, the comparison of the analysis results, etc. are executed by the analyzing system terminal device 50.

Still further, if it is desired to analyze the neighborhoods of the points to be analyzed A to F in a concentrated manner, the coordinates in the proximity of the points to be analyzed (X=XO, Y=YO) stated above may be registered according to the following equations:

$$Xn = XO - n\Delta X \ (n=1, 2, 3, \ldots) \quad (1)$$

$$Xm = YO + m\Delta Y \ (m=1, 2, 3, \ldots) \quad (2)$$

As explained above, the embodiments described above are characterized by

① means for inputting the analyzing procedure;
② means for registering the analyzing procedure;
③ control means for controlling the operation of each of the apparatuses according the analyzing procedure;
④ means for storing the analysis results obtained by means of the various analyzing apparatuses; and
⑤ means for determining and displaying the final analysis result on the basis of the analysis results thus obtained which are disposed in either one of the apparatuses constituting the system all together or dispersedly in a plurality of apparatuses, and each of these apparatuses is provided with an interface for exchange of various sorts of signals therebetween.

As the result, since a plurality of sorts of apparatuses can be controlled collectively and further the analysis results can be dealt with as a block, it is possible to improve the operability of the system and to reduce the load of the operator.

Further, although, in the embodiments described above, the case where both the collective control of a plurality of sorts of apparatuses and the collective processing of the analysis results can be realized has been explained, if it is required only to deal with the analysis results collectively and it is not required to control a plurality of sorts of apparatuses collectively, only the means indicated in ④ and ⑤ may be disposed in either one of the apparatus or dispersedly in the plurality of apparatuses.

As it is clear from the above explanation, according to the present invention, the effects as described below can be obtained.

(1) All the analyzing apparatuses can be controlled collectively, which improves the operability.

(2) Since the analysis results obtained by means of the different analyzing apparatuses can be dealt with, the analysis can be effected with a high precision without troubling the operator.

(3) Since the analysis can be executed automatically for a number of positions, the period of time, during which the operator is bound thereon, is shortened.

(4) If the analyzing system terminal device such as a computer is connected with the interfaces so that the processing of the analysis results and the control of the various apparatuses can be effected therethrough, the processing and the control more complicated of higher degree become possible.

We claim:

1. An electron microscope comprising:
means for generating an electron beam;
means of irradiating a sample with said electron beam;

a plurality of sorts of analyzing means, which detect signals obtained from said sample while irradiating it with said electron beam to analyze said sample;

means for displacing said sample;

means for inputting information identifying a plurality of predetermined positions, where said sample should be analyzed, and a procedure for analyzing said sample;

means for registering the information identifying said positions to be analyzed as well as means used therefor and the analyzing procedure thus inputted;

means for automatically controlling said sample displacing means and said plurality of sorts of analyzing means on the basis of information registered in said registering means so as to analyze all of said positions to be analyzed one after another according to said registered analyzing procedure; and means for collecting analysis results for said sample obtained by means of said plurality of sorts of analyzing means to compare these analysis results thus collected.

2. An electron microscope according to claim 1, wherein said analyzing means includes X-ray analyzing means and electron beam energy analyzing means, said X-ray analyzing means having means for obtaining variations in the intensity of characteristic X-rays generated by irradiating said sample with said electron beam depending on the energy, said electron beam energy analyzing means having means for obtaining variations in the intensity of electron beams transmitted by said sample depending on the energy, thereof when it is irradiated with said electron beam.

3. An electron microscope comprising:

means for generating an electron beam;

means for irradiating a sample with said electron beam;

a plurality of sorts of analyzing means, which detect information signals characterizing said sample, which are obtained by irradiating said sample with said electron beam to analyze elements contained in said sample;

means for displacing said sample;

means for inputting information identifying a plurality of predetermined positions, where said sample should be analyzed, and a procedure for analyzing said sample;

means for registering inputted information identifying said positions to be analyzed and the analyzing procedure thus inputted;

means for automatically controlling said sample displacing means and at least one of said plurality of analyzing means so as to analyze all of said positions to be analyzed one after another according to said registered analyzing procedure; and means for collecting analysis results obtained by means of said plurality of sorts of analyzing means to compare these analysis results thus collected, said analysis result collecting and comparing means outputting information relating to elements, which can be analyzed in common by said plurality of sorts of analyzing means and information relating to elements, which can be analyzed properly thereto by said plurality of sorts of analyzing means.

4. An electron microscope according to claim 3, wherein said analyzing means includes X-ray analyzing means and electron beam energy analyzing means, said X-ray analyzing means having means for obtaining variations in the intensity of characteristic X-rays generated by irradiating said sample with said electron beam depending on the energy, said electron beam energy analyzing means having means for obtaining variations in the intensity of electron beams transmitted by said sample depending on the energy, when it is irradiated with said electron beam.

* * * * *